United States Patent [19]
Nakamoto et al.

[11] Patent Number: 5,325,168
[45] Date of Patent: Jun. 28, 1994

[54] APPARATUS AND METHOD FOR ANALYZING CELLS IN URINE

[75] Inventors: Hiroyuki Nakamoto; Tokuhiro Okada, both of Hyogo, Japan

[73] Assignee: TOA Medical Electronics Co., Ltd., Kobe, Japan

[21] Appl. No.: 882,305

[22] Filed: May 13, 1992

[30] Foreign Application Priority Data

May 14, 1991 [JP] Japan .................................. 3-108045

[51] Int. Cl.$^5$ ..................... G01N 15/02; G01N 21/47; G01N 21/64
[52] U.S. Cl. ........................................ 356/73; 356/336; 356/338; 356/417; 209/581; 209/582; 209/939
[58] Field of Search ................ 356/72, 73, 317, 336, 356/338, 417; 250/461.2; 209/580, 581, 582, 939; 422/68.1, 82.05, 82.08, 28.09; 435/291, 808

[56] References Cited

U.S. PATENT DOCUMENTS

| | | | |
|---|---|---|---|
| 3,675,768 | 7/1972 | Legorreta-Sanchez | 356/39 |
| 3,824,402 | 7/1974 | Mullaney et al. | 356/73 |
| 3,916,197 | 10/1975 | Fulwyler | 250/304 |
| 4,263,508 | 4/1981 | Leary et al. | 356/335 |
| 4,338,024 | 7/1982 | Bolz et al. | 356/39 |
| 4,661,913 | 4/1987 | Wu et al. | 422/68.1 |
| 4,662,742 | 5/1987 | Chupp | 356/73 |
| 4,765,737 | 8/1988 | Harris et al. | 356/73 |
| 4,986,657 | 1/1991 | Ohe | 356/73 |

FOREIGN PATENT DOCUMENTS

| | | | |
|---|---|---|---|
| 0442025 | 8/1991 | European Pat. Off. | 356/73 |
| 61-71337 | 4/1986 | Japan . | |
| 3-52573 | 8/1991 | Japan . | |

OTHER PUBLICATIONS

C. Cremer et al., "Flow Cyotmetry of chromosomes: Principles and applications in medicine and molecular biology", Optik, vol. 82, No. 1, Apr. 1989, pp. 9-18.
J. A. Steinkamp, "Flow Cytometry", Review of Scientific Instruments, vol. 55, No. 9, Sep. 1984, New York, pp. 1375-1400.

*Primary Examiner*—Robert J. Warden
*Assistant Examiner*—T. A. Trembley
*Attorney, Agent, or Firm*—Fish & Richardson

[57] ABSTRACT

A method and apparatus are provided for analyzing cells in urine. A constricted zone through which various cells contained in a urine specimen flow in single file is irradiated with light having a light beam width in the direction of cell flow of between 1 $\mu$m to 20 $\mu$m. Scattered light and fluorescent light emitted by the cells is converted into scattered-light intensity data and fluorescent light intensity data. Preferably, the individual cells have been stained with a stain such that DNA will specifically emit fluorescence. Cell diameter data is also generated from the detected scattered light. Cell judgment values are stored in a memory device, and the cells in the urine specimen are classified based upon the cell judgment values.

4 Claims, 13 Drawing Sheets

Fig. 9a
Fig. 9b
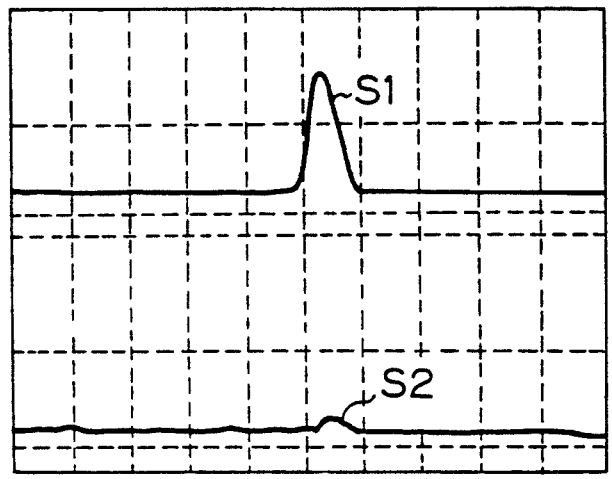
Fig. 10a
Fig. 10b
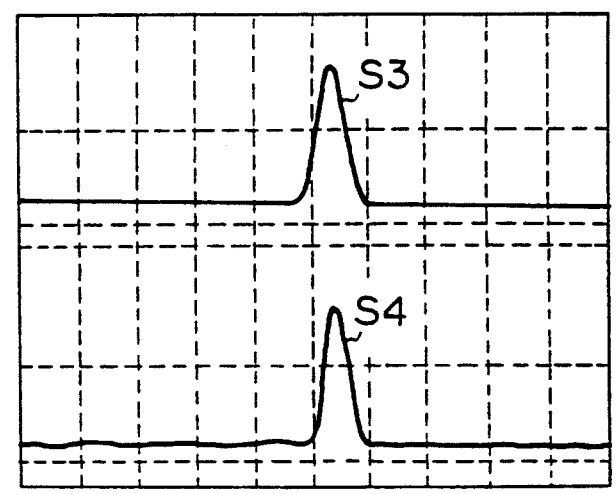

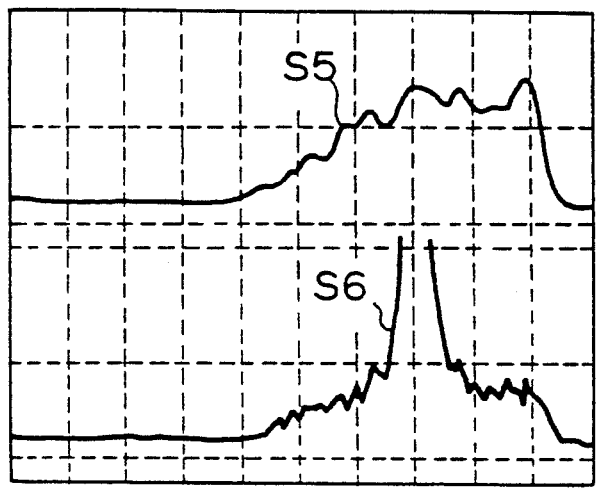
Fig. 11a
Fig. 11b
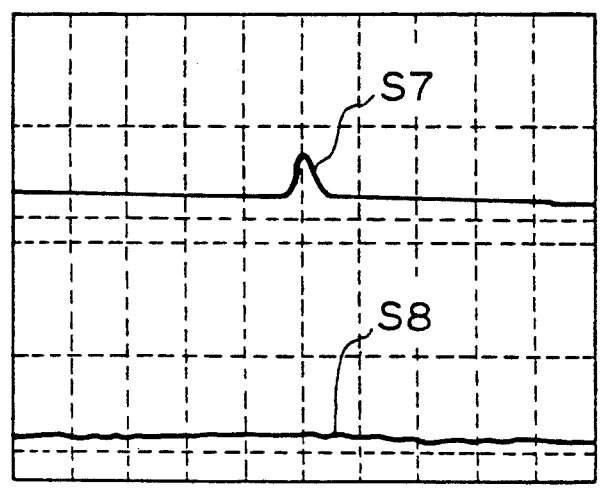
Fig. 12a
Fig. 12b

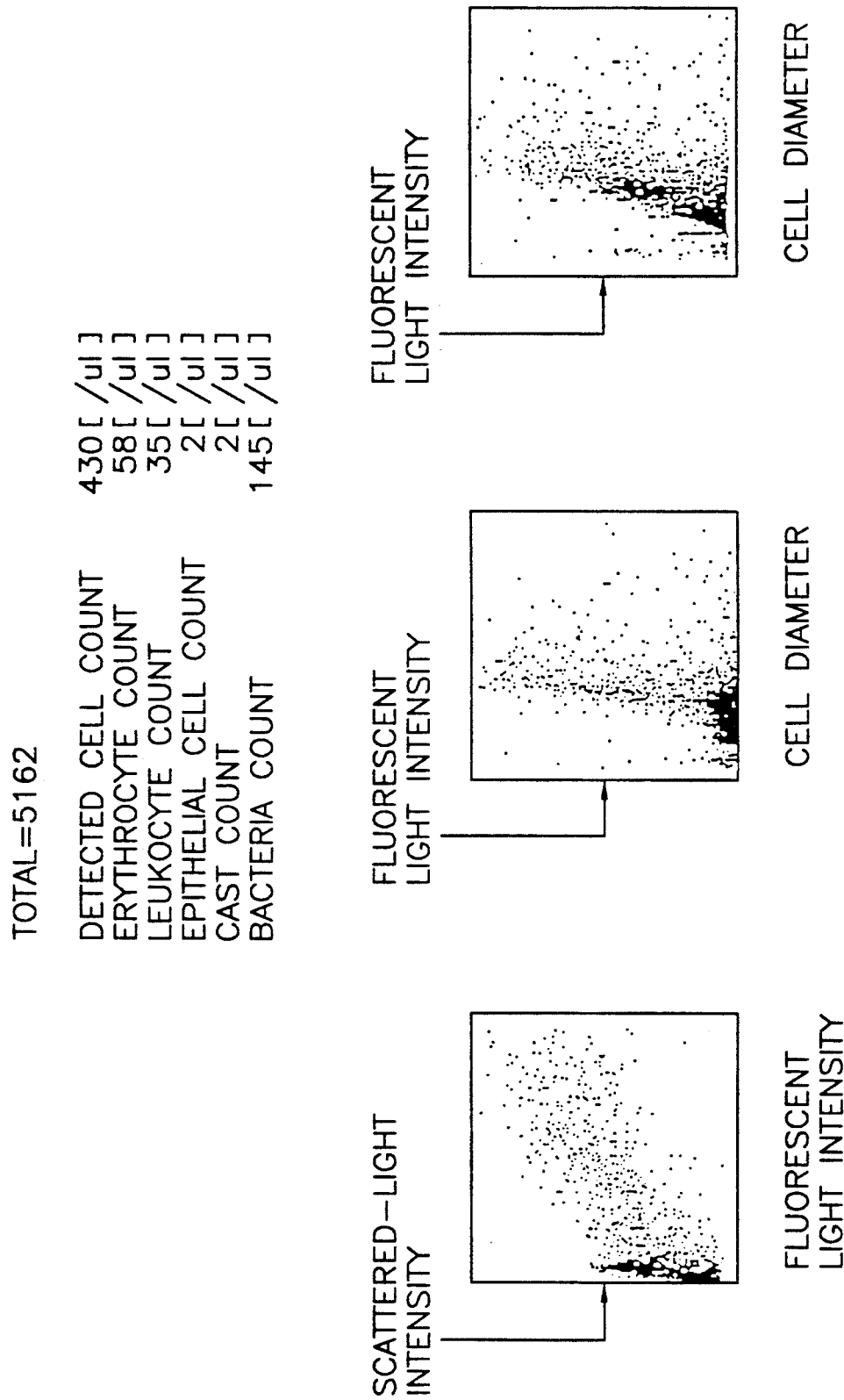

APPARATUS AND METHOD FOR ANALYZING CELLS IN URINE

BACKGROUND OF THE INVENTION

1. Field of the Invention

This invention relates to an apparatus which uses flow cytometry to classify and enumerate cells such as leukocytes, erythrocytes, epithelial cells, casts and bacteria contained in urine.

2. Description of the Prior Art

Examination of urine content has long been carried out and is still of great importance. For example, a screening test for kidney failure can be conducted based upon the presence of erythrocytes, leukocytes, epithelial cells, casts and bacteria in urine. Measurement of erythrocytes is important in terms of determining whether hemorrhage has occurred in the tract from the slomerulus to the urethra of the kidney. The appearance of leukocytes is considered to be a possible indication of a kidney disorder such as pyelonephritis, and detection thereof is important in early discovery of inflammation and infection. Furthermore, by examining cast and erythrocyte morphology, the origin of such inflammation and infection, namely the abnormal parts of the body, can be surmised.

In this specification, the word "cell" shall be used as a generic term for an erythrocyte, epithelial cell, cast and bacterium.

Conventional methods of analyzing cells in urine include (a) visual examination based upon microscopy and (b) automatic measurement using a combination of a flat sheath flow and image processing technology.

Method (a) involves centrifuging a urine specimen, preparing a slide sample of the matter of sediment and observing, classifying and counting cells under a microscope.

Method (b), an example of which is disclosed in the specification of Japanese Patent Application Laid-Open (KOKAI) No. 57-500995 or U.S. Pat. No. 4,338,024, involves using a video camera to capture an image of a urine specimen made to flow as an extremely flat stream within a sheathing solution employed as an outer layer, and subjecting the still picture obtained to image processing, whereby the images of the cells in the specimen are extracted and displayed.

However, both of the foregoing methods exhibit certain drawbacks. Specifically, method (a) which relies upon a microscope entails considerable labor for such pretreatments as centrifugal separation and staining. In addition, cells may be damaged in the centrifuging process and there are disparities in concentration from one specimen to another.

The apparatus which uses method (b) is itself high in cost owing to reliance upon image processing, and the processing speed is low. Furthermore, the advantage of automation afforded by the apparatus of method (b) merely displays the images upon roughly classifying the imaged components based upon their size, and it is required that classification process be performed by a human being while the display is observed. Thus, the automatic classification and enumeration of cell components is not possible.

Further, since the amount of the urine specimen measured according to the methods (a) and (b) is very small, a drawback is that casts, the discovery of the presence of which is very important, cannot be discovered in the urine sediment. Specifically, the low frequency of the presence of cast in such that usually only several tens thereof are present per milliliter.

Another problem is that since the types of components in urine sediment are numerous and differ widely in size from one specimen to another, and in view of the fact that the degree of cell damage can be considered to be large, it is understood that analysis of urine sediment is not possible using flow cytometry.

SUMMARY OF THE INVENTION

Accordingly, the present invention seeks to improve upon the foregoing shortcomings and its object is to provide an apparatus for analyzing cells in urine, in which a large quantity of a urine specimen can be analyzed using flow cytometry, the number of various cells (erythrocytes, leukocytes, epithelial cells, casts and bacteria, etc.) detected in the specimen can be greatly increased to enable more precise analysis of cells in urine, the process from drawing of the urine specimen into the apparatus to display of the analytical results can be fully automated to eliminate the need for any human intervention, the processing speed can be raised and the cost of the apparatus can be kept low.

According to the present invention, the foregoing object is attained by providing an apparatus for analyzing cells in urine characterized in that scattered light and fluorescent light from individual cells in a urine specimen are detected by flow cytometry, data indicative of scattered-light intensity and data indicative of fluorescent-light intensity is obtained from the scattered light and fluorescent light, the scattered light is converted into pulse signals, and the pulse width is converted into cell-diameter data in accordance with known cell diameters. The apparatus is further characterized in that actual-measurement data indicating the characteristics of each cell is stored in memory beforehand as cell judgment values, and the data indicative of the detected cells is analyzed in accordance with these cell judgment values.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 9 is a waveform diagram in which (a) illustrates an output waveform of a forward-scattered light signal from an erythrocyte and (b) illustrates an output waveform of a forward fluorescent-light signal from the erythrocyte;

FIG. 10 is a waveform diagram in which (a) illustrates an output waveform of a forward-scattered light signal from a leukocyte and (b) illustrates an output waveform of a forward fluorescent-light signal from the leukocyte;

FIG. 11 is a waveform diagram in which (a) illustrates an output waveform of a forward-scattered light signal from an epithelial cell and (b) illustrates an output waveform of a forward fluorescent-light signal from the epithelial cell;

FIG. 12 is a waveform diagram in which (a) illustrates an output waveform of a forward-scattered light signal from a bacterium and (b) illustrates an output waveform of a forward fluorescent-light signal from the bacterium;

FIG. 14 illustrates scatter diagrams in which (a) is a scatter diagram of side-scattered light intensity and fluorescent light intensity, (b) a scatter diagram of fluorescent light intensity and cell diameter and (c) a scatter diagram of scattered-light intensity and cell diameter.

DETAILED DESCRIPTION OF THE PREFERRED EMBODIMENT

A preferred embodiment of an apparatus for analyzing cells in urine according to the present invention will now be described with reference to the drawings.

Figure 1:
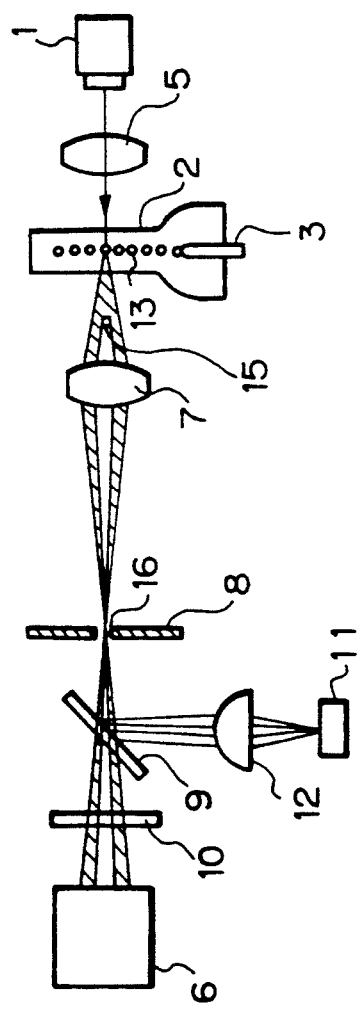
FIG. 1 is a block diagram showing the arrangement of the principal elements of an optical system embodying the present invention.

FIG. 1 is a block diagram showing the arrangement of the principal elements of an optical system embodying the present invention. As shown in FIG. 1, the optical system includes a light source 1 constituted by an argon-ion laser at one end of the system, a flow cell 2, a condenser lens 5 provided between the light source 1 and the flow cell 2, a photomultiplier 6 at the other end of the system, a collector lens 7, a light shield 8, a dichroic mirror 9 and a filter 10 provided between the flow cell 2 and the photomultiplier 6, and a lens 12 provided between the dichroic mirror 9 and a photodiode 11. A urine specimen flows into the flow cell 2 from a nozzle 3 attached to the flow cell. Reference numeral 15 denotes a beam stopper.

Figure 2:
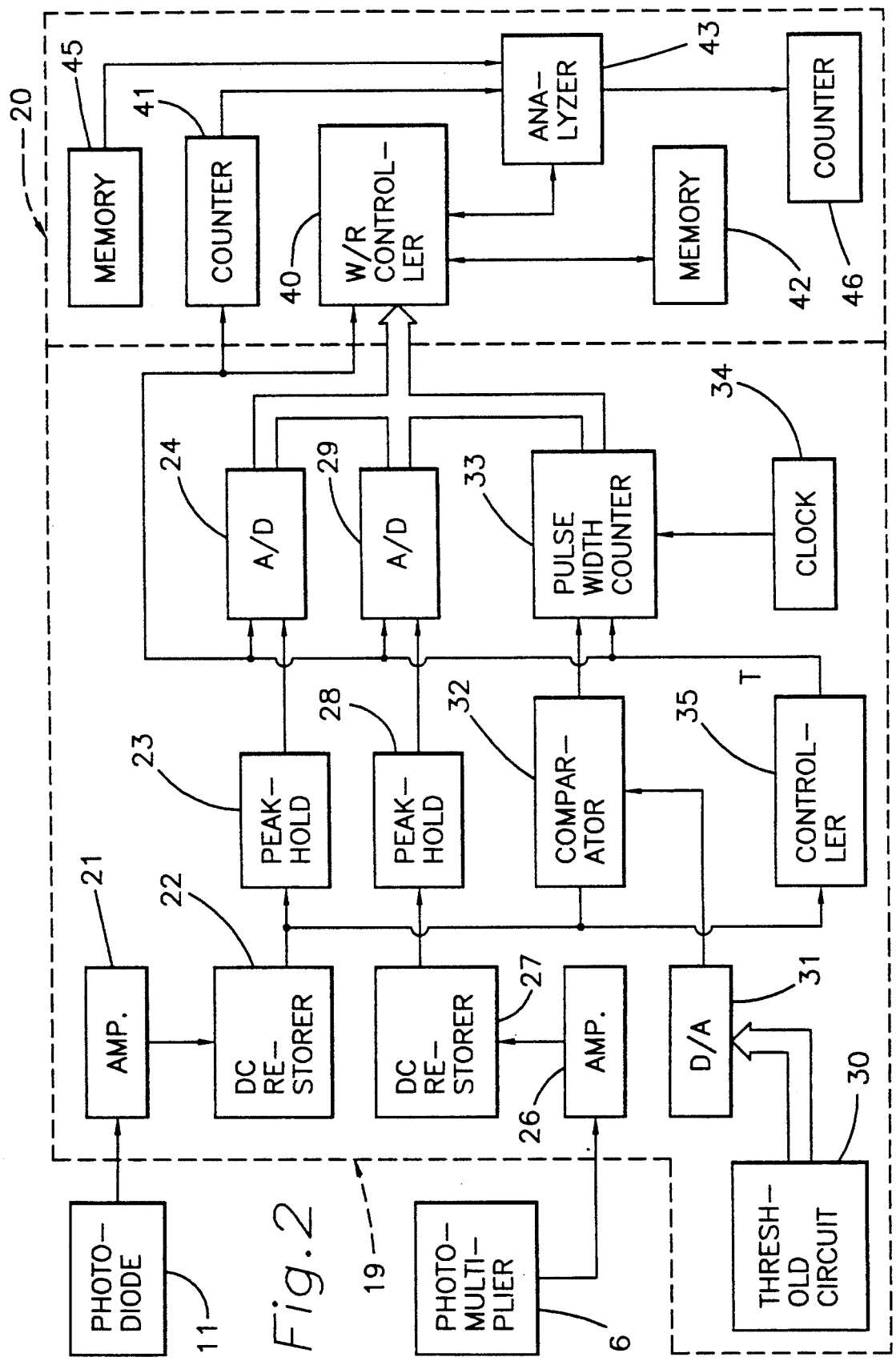
FIG. 2 is a block diagram illustrating the principal components of an electric circuit embodying the present invention.
Figure 3A:
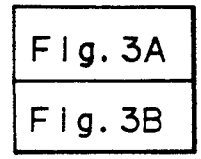
FIGS. 3A–3B are a flowchart illustrating operation of the embodiment.
Figure 3A:
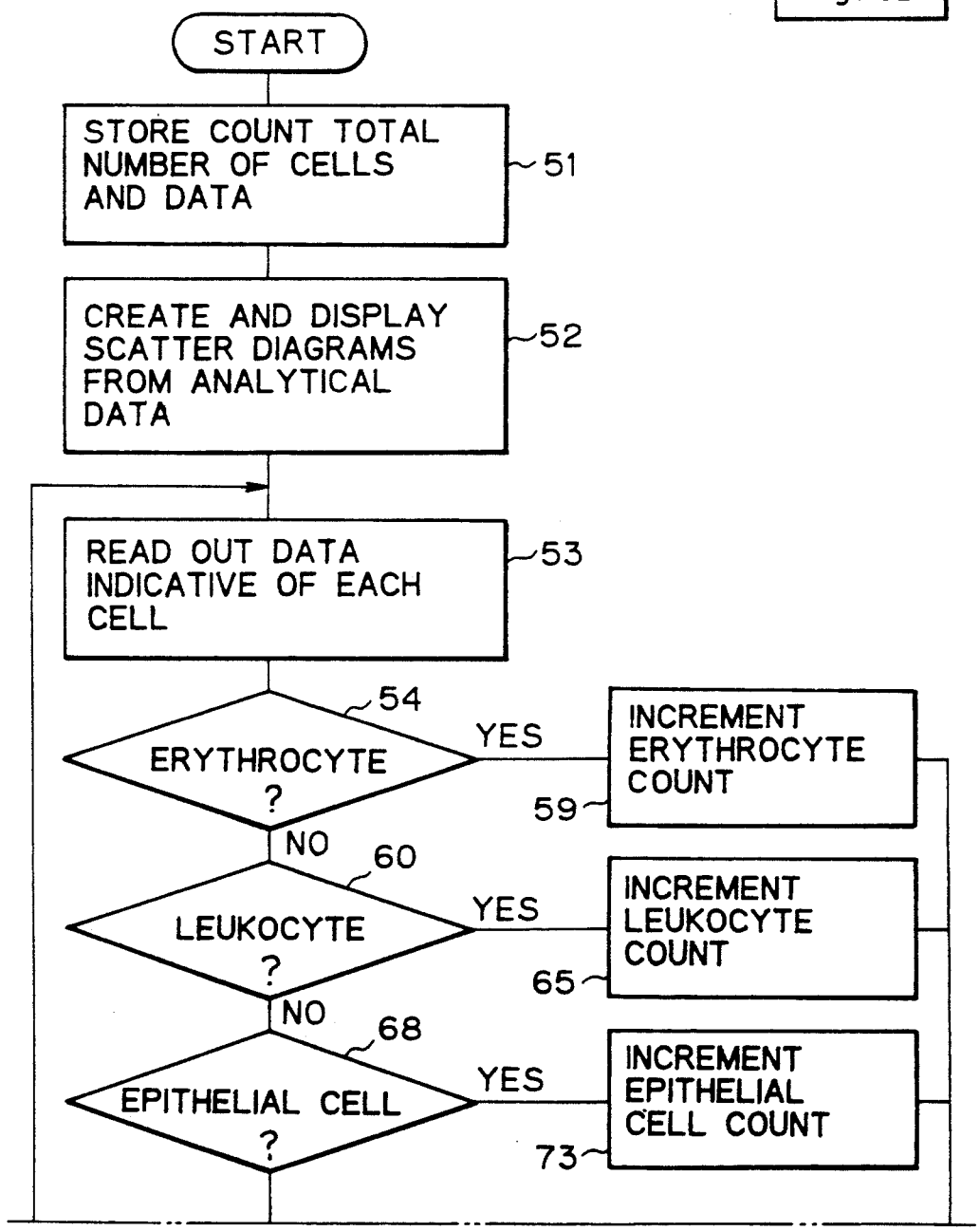
Figure 3B:
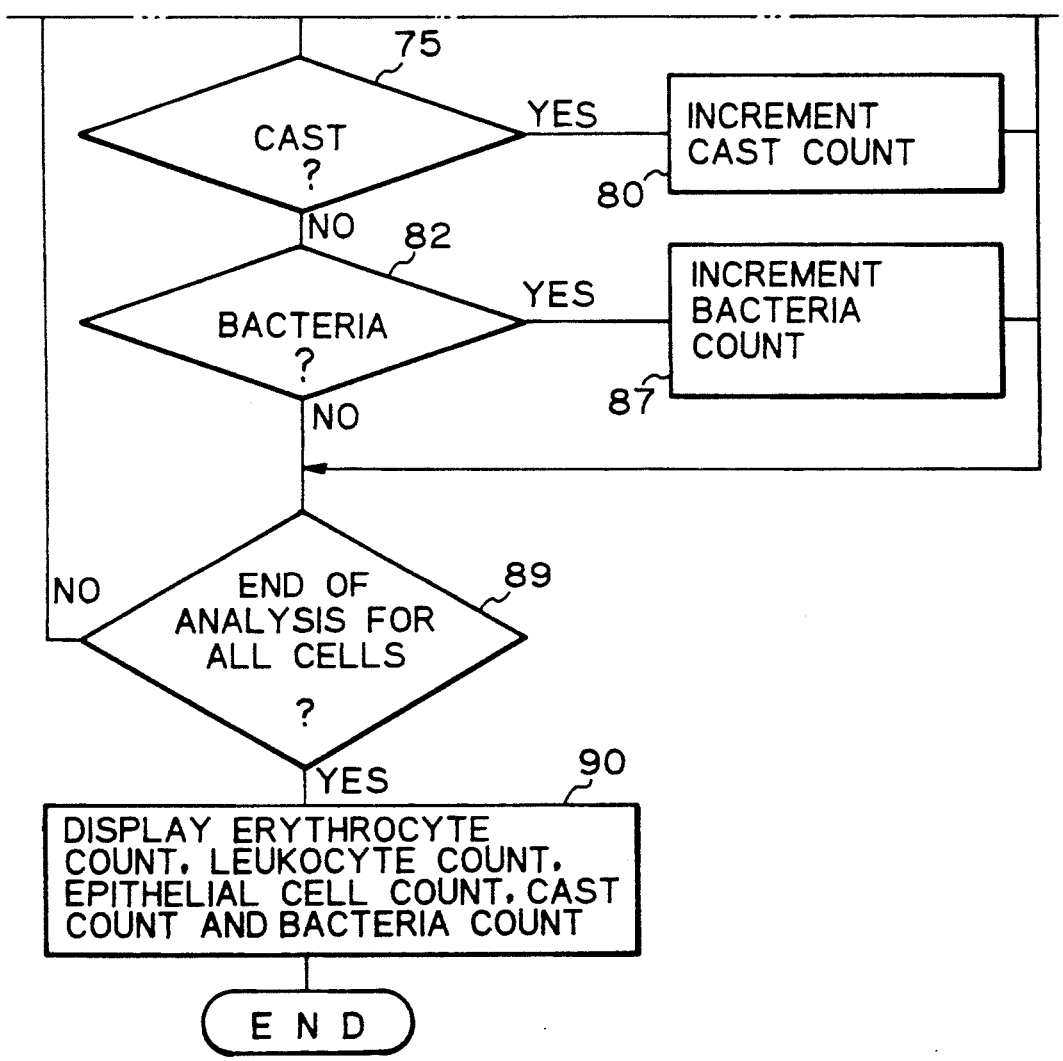
Figure 4:
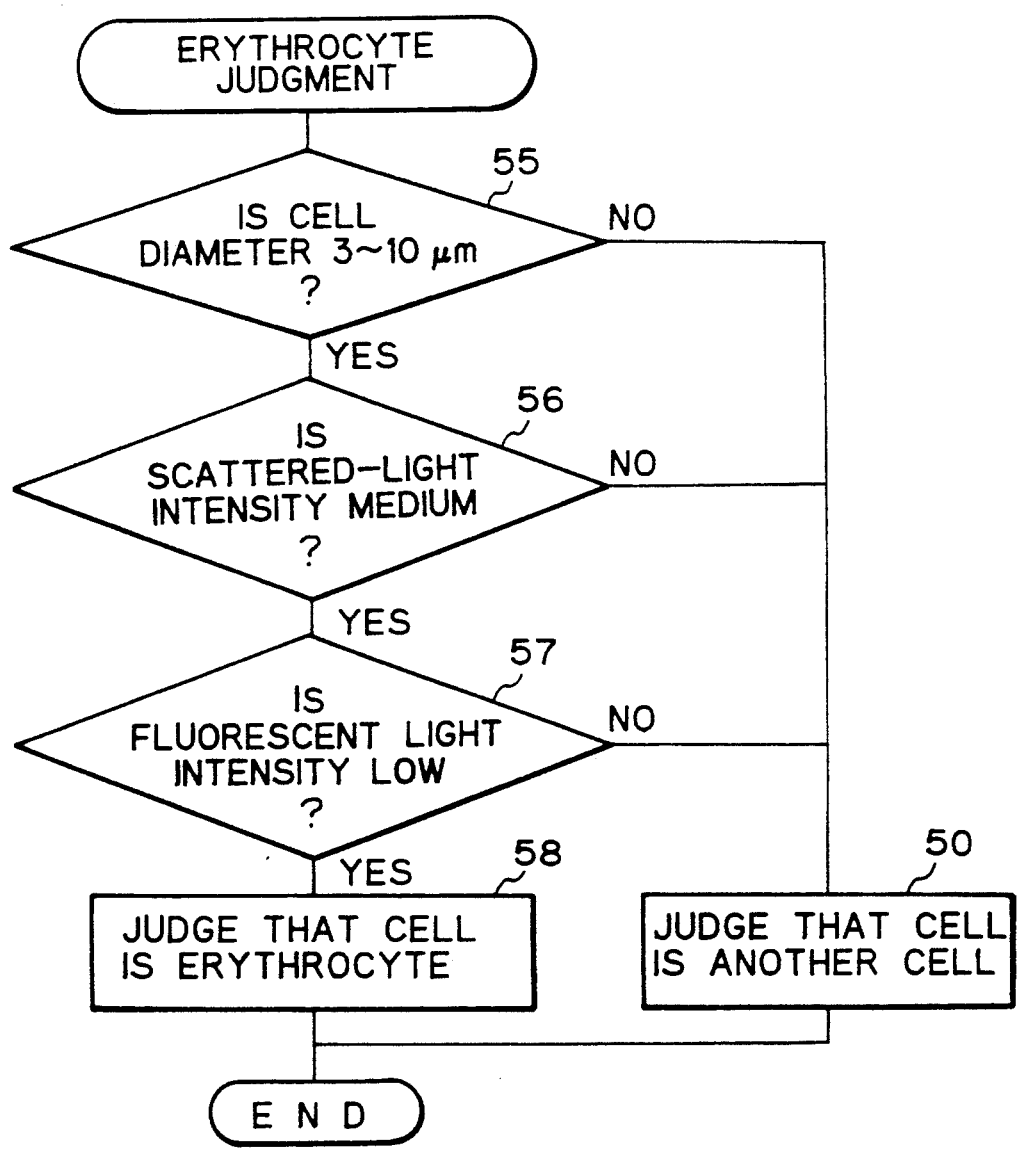
FIG. 4 is a flowchart illustrating an operation for analyzing erythrocytes according to the embodiment.
Figure 5:
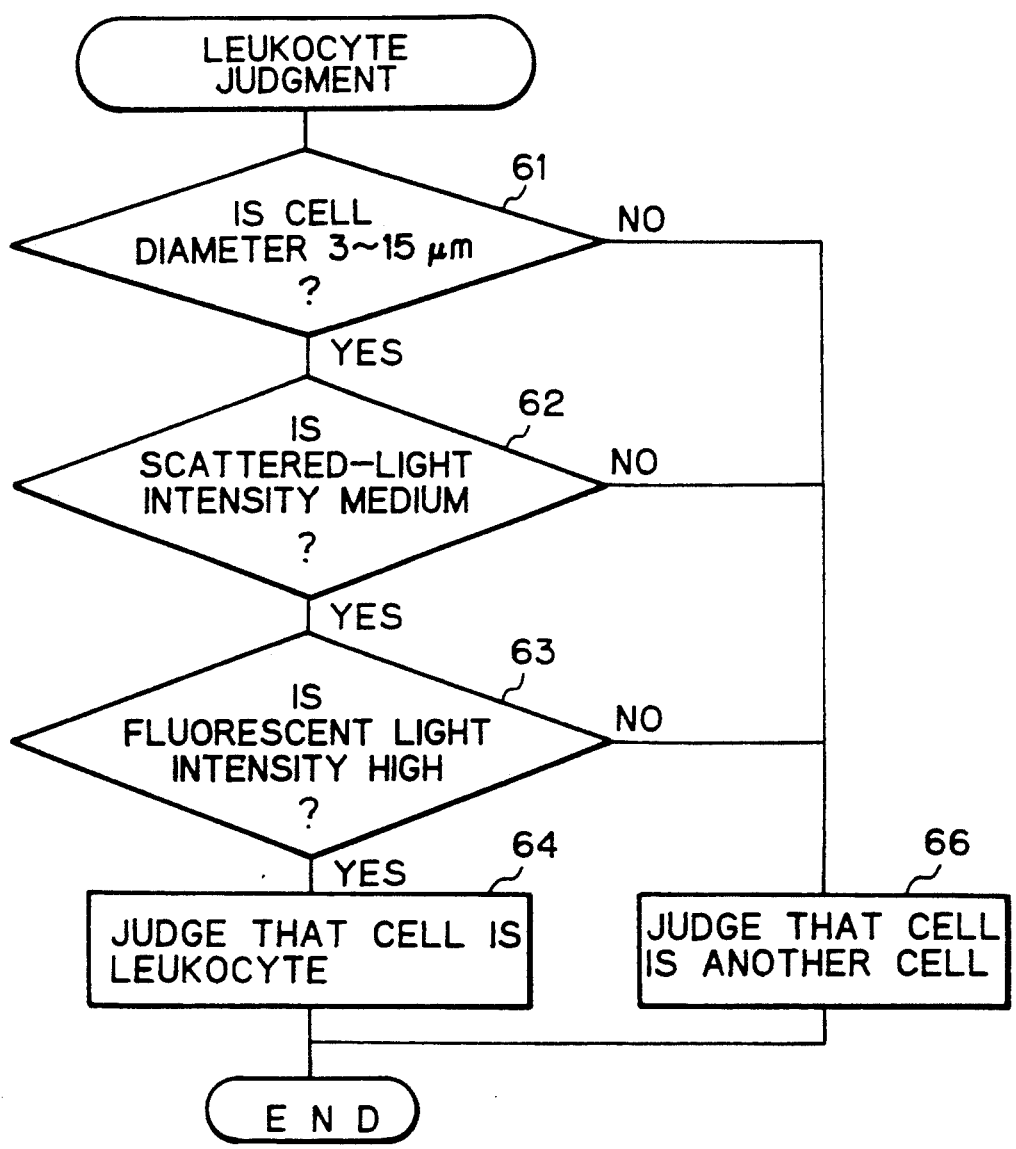
FIG. 5 is a flowchart illustrating an operation for analyzing leukocytes according to the embodiment.
Figure 6:
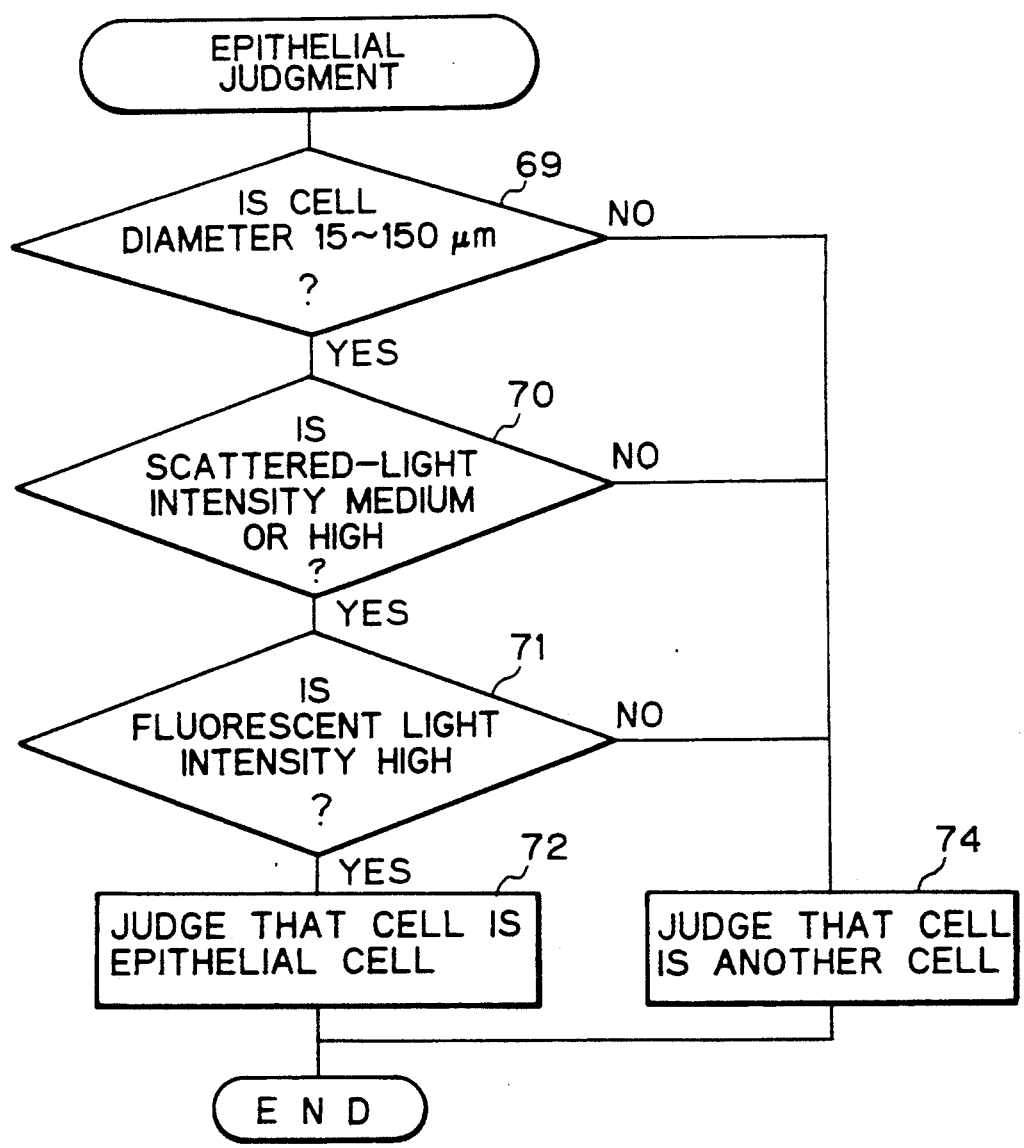
FIG. 6 is a flowchart illustrating an operation for analyzing epithelial cells according to the embodiment.
Figure 7:
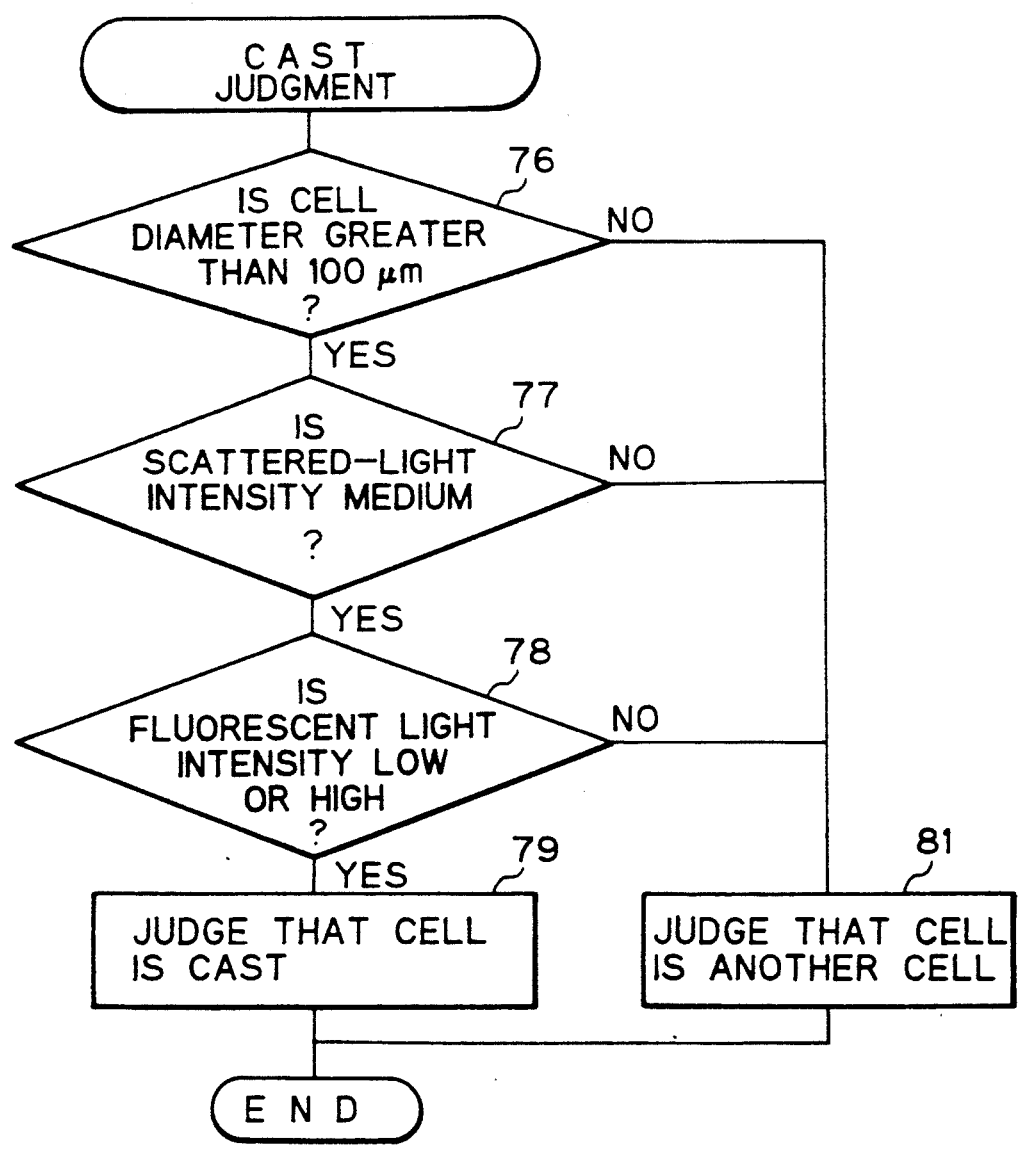
FIG. 7 is a flowchart illustrating an operation for analyzing casts according to the embodiment.
Figure 8:
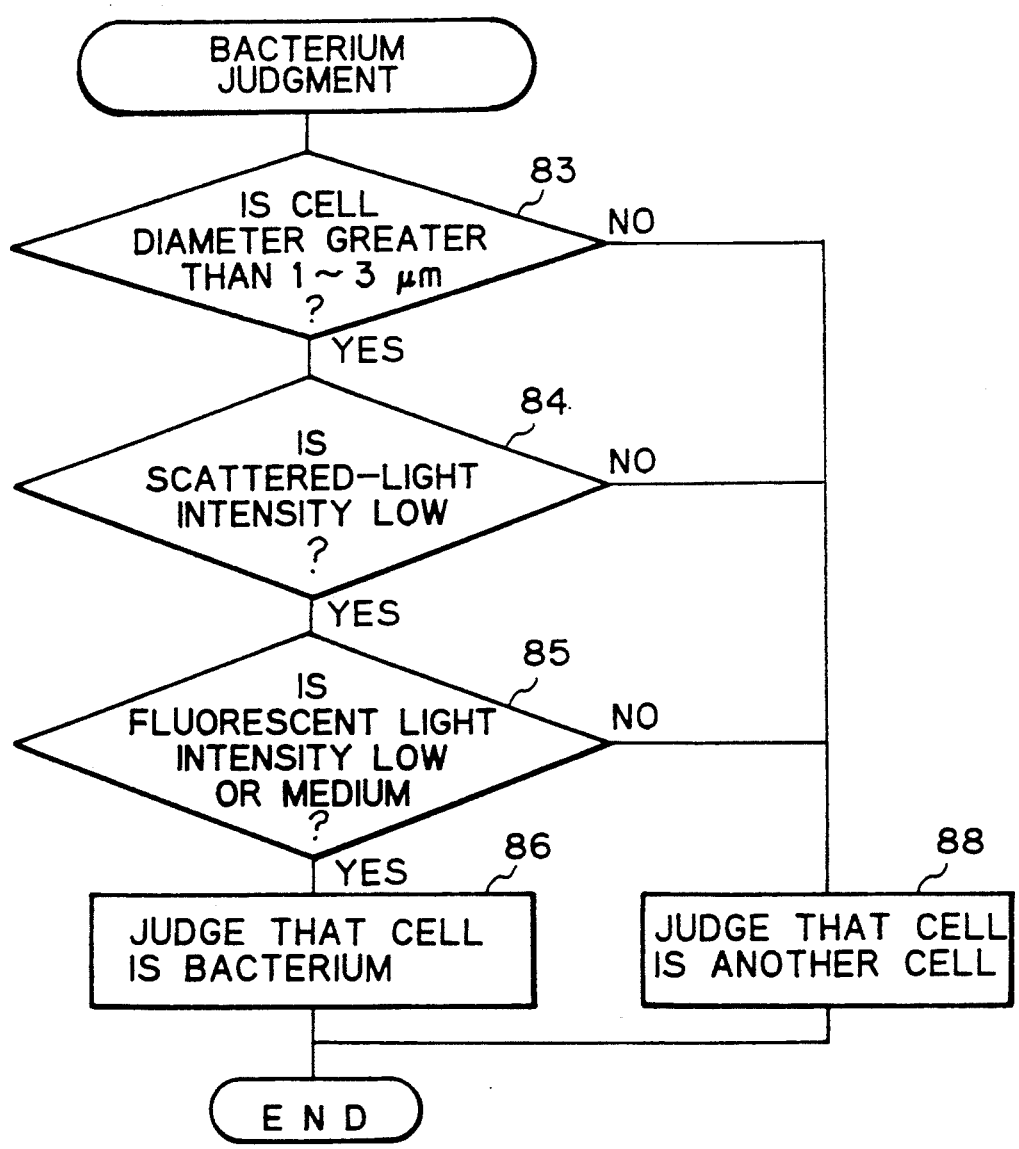
FIG. 8 is a flowchart illustrating an operation for analyzing bacteria according to the embodiment.

FIG. 2 is a block diagram illustrating the principal components of an electric circuit embodying the present invention.

The circuitry of FIG. 2 is divided into a signal processing portion 19 and data processing portion 20. An output signal from the photodiode 11 is connected to an amplifier 21 in the signal processing portion 19, and the output of the amplifier 21 is connected to a DC (direct-current) restorer 22. The output of the DC restorer 22 is connected to a peak-hold circuit 23, the output of which is connected to an analog/digital converter circuit (hereinafter referred to simply as an "A/D converter") 24.

The output of the photomultiplier 6 is connected to an amplifier 26 in the signal processing portion 19, the output of which is connected to a DC (direct-current) restorer 27. The output of the latter is connected to a peak-hold circuit 28, the output of which is connected to and A/D (analog/digital) converter 29.

Further, a threshold circuit 30 is connected to a digital/analog converter circuit (hereinafter referred to simply as a "D/A converter") 31, the output of which is connected to the reference input of a comparator 32. The output of the DC restorer 22 is connected to the comparator 32 at its other input terminal, namely the terminal whose input is to be compared with the reference. The output of the comparator 32 is connected to a pulse-width counter 33, to which a clock signal output from a clock signal generating circuit 34 is applied as an input. The output of the DC restorer 22 is further connected to a control circuit 35. The latter produces a control signal output connected to the A/D converters 24, 29 and to the pulse-width counter 33.

The outputs of the A/D converters 24, 29 and the output of the pulse-width counter 33 are connected to a control circuit 40 for controlling a read/write operation. A trigger signal T is connected to the control circuit 40 and a counter 41. A memory circuit 42 for storing data indicative of individual cells is connected to the control circuit 40. The memory circuit 42 is connected, via the control circuit 40, to a data analyzing circuit 43 which classifies and enumerates cells. The output of the counter 41 also is connected to the data analyzing circuit 43. A memory circuit 45 which stores the control program of the apparatus, cell-diameter conversion values, cell judgment values, etc., and a counter 46, which counts the number of each type of cell, are connected to the data analyzing circuit 43.

FIGS. 3 through 8 are flowcharts illustrating the operation of the electrical circuitry according to this embodiment. These flowcharts will be referred to later.

The operation which characterizes the embodiment of the invention constructed as set forth above will now be described.

The original solution of the urine specimen contains in admixture a first reagent containing a specific stain and a second reagent for stabilizing pH and osmotic pressure. The resulting urine specimen mixture containing the reagent is discharged from the nozzle 3, and a sheathed flow is formed by causing a sheathing solution to flow along the periphery of the urine stream. As a consequence, cells 13 (erythrocytes, leukocytes, epithelial cells, casts and bacteria, etc.) in the urine specimen flow in an ordered array such as in single file through a narrow zone at the central portion of the flow cell 2, as shown in FIG. 1. The laser light from the light source 1 is condensed by the condenser lens 5 so as to irradiate the narrow flow zone of the flow cell with an elliptical beam spot that is slender in the direction of flow and broad in the direction perpendicular to the flow direction.

The present invention is directed toward measurement of cells in urine, namely components of urine sediment. In order to obtain more detailed information from the group of cells carried by urine, the thickness of the narrow flow zone should be set to be comparatively small in comparison with the sizes of the cells. As for the dimensions of the irradiating elliptical beam spot at the constricted portion of the specimen stream, a suitable value for the minor axis of ellipse is 1–20 $\mu$m. It will suffice to make the major axis of the ellipse large enough to fully extend across the width of the slender specimen stream in the narrow flow zone.

Thus, the cells 13 in the slender specimen stream are irradiated with the laser light. Transmitted laser light which has passed through the flow cell intact without striking the cells is blocked by a beam stopper 15. Forward-scattered light and forward fluorescent light emitted from an irradiated cell at a narrow angle is condensed by the collector lens 7, and the condensed light passes through a pin hole 16 of the shield 8. Almost all of the forward-scattered light and forward fluorescent light thus emitted from the cell 13 arrives at the dichroic mirror 9. The fluorescent light, the wavelength of which is greater than that of the scattered light, is transmitted intact by the dichroic mirror 9 at a high rate and stray light is removed by the filter 10, after which the fluorescent light is detected and converted into an electric signal by the photomultiplier 6, from which a forward fluorescent light signal is outputted. Meanwhile, the scattered light is reflected by the dichroic mirror 9 at a high rate, after which the light is condensed by the lens 12 and converted into an electric signal by the photodiode 11, from which a forward-scattered light signal is outputted.

Output waveforms of the forward-scattered light signal from the photodiode 11 and output waveforms of the forward fluorescent-light signal from the photomultiplier 6 are as illustrated in the waveform diagrams of FIGS. 9 through 13, in which time is plotted along the horizontal axis and voltage along the vertical axis.

In FIG. 9, (a) shows the output waveform of a forward-scattered light signal from an erythrocyte and (b) shows an output waveform of a forward fluorescent-light signal from the erythrocyte. Since erythrocytes are small in size and regular in shape, a forward-scattered light signal $S_1$ having a single peak is obtained. However, since an erythrocyte does not possess a nucleus, it cannot be stained by a stain and therefore fluorescent light $S_2$ is not detected.

In FIG. 10, (a) shows the output waveform of a forward-scattered light signal from a leukocyte and (b) shows an output waveform of a forward fluorescent-light signal from the leukocyte. Leukocytes are large but are of the same size or slightly larger than erythrocytes, and a forward-scattered light signal $S_3$ similar to the forward-scattered light signal $S_1$ is detected. However, a forward fluorescent-light signal $S_4$ also is detected owing to the presence of a nucleus.

In FIG. 11, (a) shows the output waveform of a forward-scattered light signal from an epithelial cell and (b) shows an output waveform of a forward fluorescent-light signal from the epithelial cell. Epithelial cells exist in a wide variety of sizes from large to small, but they are small in thickness and possess a complicated shape and internal structure. As a result, a forward-scattered light signal $S_5$ obtained exhibits a large width and a complicated waveform. Since the minor axis of the beam spot of the irradiating light is smaller than the diameter of an epithelial cell, the signal waveform obtained reflects the size, shape and internal structure of the cell. However, in comparison with the forward-scattered light signal $S_1$ of the erythrocyte and the forward-scattered light signal $S_3$ of the leukocyte, the forward-scattered light signal $S_5$ of the epithelial cell does not have a peak value which is that high in proportion to the large width of the signal. The reason for this is understood to be that since the cell thickness is small, all of the irradiating light is not scattered; i.e., some of it transmitted through the cell. Further, a forward fluorescent-light signal $S_6$ obtained also has a large width and a complicated waveform. The portion of the waveform at which signal strength is very high represents the location of the nucleus. Epithelial cells have a large amount of cytoplasm, which also emits a certain degree of fluorescence.

In FIG. 12, (a) shows the output waveform of a forward-scattered light signal from a bacterium and (b) shows an output waveform of a forward fluorescent-light signal from the bacterium. Since bacteria are small in comparison with blood cells and the like, a small forward-scattered light signal $S_7$ and forward fluorescent-light signal $S_8$ are detected.

Figures 13A, 13B:
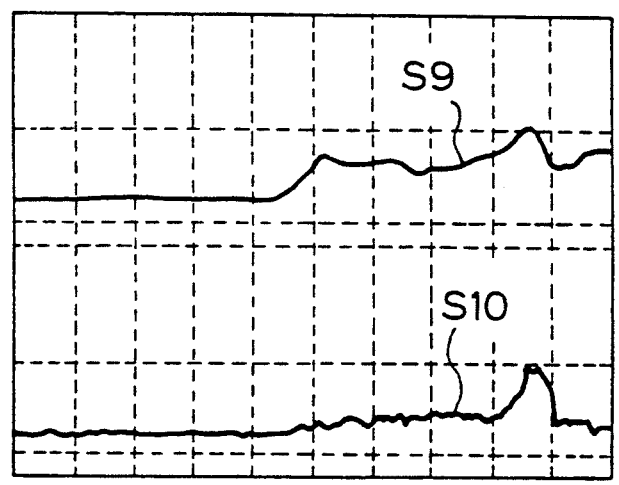
FIG. 13 is a waveform diagram in which (a) illustrates an output waveform of a forward-scattered light signal from a cast and (b) illustrates an output waveform of a forward fluorescent-light signal from the cast.

In FIG. 13, (a) shows the output waveform of a forward-scattered light signal from a cast and (b) shows an output waveform of a forward fluorescent-light signal from the cast. Since a cast has a size on the order of one hundred to several hundred microns, a forward-scattered light signal $S_9$ and a forward fluorescent-light signal $S_{10}$ having a very large width are obtained.

Thus, the photomultiplier 6 produces a forward fluorescent-light signal for each of the variety of cells contained in the urine specimen. Each forward fluorescent-light signal is amplified by the amplifier 26 in the signal processing portion 19, and the amplified signal is applied to the DC restorer 27, which removes DC components and extracts the amplitude portion (namely the portion of the forward fluorescent-light signal). The resulting forward fluorescent-light signal from which the DC components have been removed is applied to the peak-hold circuit 28, which detects the peak value of the signal. The detected peak value is converted into a digital value by A/D converter 29, and this value is outputted as data indicative of the intensity of forward fluorescent light.

The photodiode 11 produces a forward-scattered light signal for each of the variety of cells contained in the urine specimen. Each forward-scattered light signal is amplified by the amplifier 21 in the signal processing portion 19, and the amplified signal is applied to the DC restorer 22, which removes DC components and extracts the amplitude portion (namely the portion of the forward-scattered light signal). The resulting forward-scattered light signal from which the DC components have been removed is applied to the peak-hold circuit 23, which detects the peak value of the signal. The detected peak value is converted into a digital value by the A/D converter 24, and this value is outputted as data indicative of the intensity of forward-scattered light. The resulting forward-scattered light signal from which the DC components have been removed is applied to the comparison input terminal of the comparator 32.

In order to eliminate the effects of contaminants such as dust particles contained in the urine specimen, the threshold circuit 30 is set beforehand to an appropriate threshold value. This value is converted into an analog value by the D/A converter 31, and a voltage indicative of the analog value is applied to the reference input terminal of the comparator 32. Only a forward-scattered light signal which exceeds the threshold value is outputted by the comparator 32 in the form of square wave. The square-wave signal enters the pulse-width counter 33, which counts the clock signal from the clock signal generator 34 for the duration of the square wave-input. As a result, the forward-scattered light signal is converted into pulse-width data, which is outputted by the pulse-width counter 33. At this time the output of the DC restorer 22 enters the control circuit 35, which proceeds to detect the beginning and end of the forward-scattered light signal and control the duration of the pulse width count performed by the pulse-width counter 33. Accordingly, each item of pulse-width data is data which corresponds to the cell diameter of each detected cell. Further, the above-mentioned control signal from the control circuit 35 is applied also to the A/D converters 24 and 29, and the A/D converters 24, 29 respectively output data indicative of the forward-scattered light intensity and data indicative of the forward fluorescent-light intensity for each and every cell, as described above.

In accordance with the invention, a measurement is taken using latex particles of a known particle diameter before a urine specimen is measured. Then, from the pulse-width data acquired by this preliminary measurement of the latex particles and the known diameter of these particles, conversion values for the purpose of converting the above-mentioned pulse-width data into particle diameters are calculated and the conversion values are then stored in the memory circuit 45 beforehand as conversion values of cell diameter.

Furthermore, the erythrocytes, leukocytes, epithelial cells, casts and bacteria contained in a urine specimen are actually measured, and the characteristics of each cell statistically decided based upon these actual measurements are stored in the memory circuit 45 as cell judgment values of the kind shown in the table below.

TABLE

| | Cell Diameter | Scattered-Light Intensity | Fluorescent-Light Intensity |
|---|---|---|---|
| Erythrocytes | 3–10 μm | Medium | Low |
| Leukocytes | 3–15 μm | Medium | High |
| Epithelial Cells | 15–150 μm | High.Medium | High |
| Casts | Above 100 μm | Medium | Low.High |
| Bacteria | 1–3 μm | Low | Medium.Low |

In the table, the cell diameters are values decided statistically upon actually measuring the erythrocytes, leukocytes, epithelial cells, casts and bacteria in a urine specimen using a microscope. The intensity of forward-scattered light reflects a plurality of items of information, such as cell size, density and surface configuration. There are cells (epithelial cells) for which the intensity of scattered light is high, cells (erythrocytes, leukocytes, casts and some epithelial cells) for which the intensity is medium, and cells (bacteria) for which the intensity is low. The intensity of the fluorescent light is information proportional to the amount of DNA. There are cells (leukocytes, epithelial cells and casts in which cells are sealed) for which the intensity of fluorescent light is high, cells (bacteria) for which the intensity is medium, and cells (bacteria, erythrocytes, hyaline casts) for which the intensity is low. The reason for the low fluorescent intensity of glass casts is that these do not contain DNA. In addition, though bacteria contain DNA, the cells are small in size and therefore the amount of DNA content is small in comparison with other cells. The intensity of fluorescent light also is medium or low.

Under these conditions, the items of forward-scattered light intensity data, forward fluorescent-light intensity data and pulse-width data associated with each cell are stored, on a cell-by-cell basis, in the memory circuit 42 whenever the trigger signal T, which is generated at each cell flow-by, enters the data processing portion 20. The pulse-width data is converted into cell-diameter data by the data analyzer 43 based upon the aforementioned cell diameter conversion values, and the cell-diameter data obtained is stored in the memory circuit 42. The counter 41 counts the cells in successive fashion. This operation is carried out until the entirety of the urine specimen has passed through the flow cell 2. The storage and counting operations are executed at step 51 in the flowchart of FIG. 3. When all of the urine specimen has passed through the flow cell 2, the total number of cells detected in the urine specimen is held in the counter 41, and the items of forward-scattered light intensity data, forward fluorescent-light intensity data and cell-diameter data associated with each cell detected in the urine specimen are stored in the memory circuit 42.

Under these conditions, the data analyzer 43 reads the data for all cells out of the memory circuit 42 and then creates and displays various scatter diagrams (a), (b) and (c) shown in the upper part of FIG. 14 (step 52). Observing the scatter diagrams of FIG. 14 makes it possible for the user to judge at a glance whether the results of urinalysis are normal or abnormal. In addition, the user can easily verify whether the scatter diagrams of FIG. 14 are indicative of patterns of an abnormal specimen. If the specimen is normal, almost no cells will appear in the scatter diagram. In FIG. 14, (a) is a scatter diagram of scattered light intensity and fluorescent light intensity, (b) a scatter diagram of fluorescent light intensity and cell diameter and (c) a scatter diagram of scattered-light intensity and cell diameter.

Each item of cell data is read out of the memory circuit 42 (step 53), and each cell is analyzed by the data analyzer 43 in accordance with the cell judgment data in the memory 45. More specifically, if the data indicative of the diameter of the read cell is 3–10 μm, the scattered-light intensity data is medium and the fluorescence intensity data is low, then the cell is judged to be an erythrocyte (steps 54–58). When a cell is judged to be an erythrocyte, the counter 46 increments the erythrocyte count (step 59). If the cell is not an erythrocyte, it is judged to be another cell (step 50).

If data indicative of the diameter of the cell judged to be another cell is 3–15 μm, the scattered-light intensity data is medium and the fluorescence intensity data is high, then the cell is judged to be a leukocyte (steps 60–64). When a cell is judged to be a leukocyte, the counter 46 increments the leukocyte count (step 65). If the cell is not a leukocyte, it is judged to be another cell (step 66).

If the data indicative of the diameter of the cell judged to be another cell is 15–150 μm, the scattered-light intensity data is high or medium and the fluorescence intensity data is high, then the cell is judged to be an epithelial cell (steps 68–72). When a cell is judged to be an epithelial cell, the counter 46 increments the epithelial cell count (step 73). If the cell is not an epithelial cell, it is judged to be another cell (step 74).

If the data indicative of the diameter of the cell judged to be another cell is greater than 100 μm, the scattered-light intensity data is medium and the fluorescence intensity data is low or high, then the cell is judged to be a cast (steps 75–79). When a cell is judged to be a cast, the counter 46 increments the cast count (step 80). If the cell is not a cast, it is judged to be another cell (step 81).

If the data indicative of the diameter of the cell judged to be another cell is 1–3 μm, the scattered-light intensity data is low and the fluorescence intensity data is medium or low, then the cell is judged to be a bacterium (steps 82–86). When a cell is judged to be a bacterium, the counter 46 increments the bacteria count (step 87). If the cell is not a bacterium, it is judged to be another cell (step 88). Cell analysis is carried out for all detected cells (step 89), the erythrocyte count, leukocyte count, epithelial cell count, cast count and bacteria count per microliter of the urine specimen are calculated, and the calculated numerical values are displayed together with the cell count below the scatter diagrams of FIG. 14 (step 90). Thus, the results of highly accurate urinalysis can be obtained.

Though the foregoing embodiment has been illustrated taking forward-scattered light and forward fluorescent light as an example, it should be obvious equally good results can be obtained using side-scattered light or side fluorescent light as well. If necessary, the display can be limited solely to the various cell counts without presenting a display of the scatter diagrams of FIG. 14.

The apparatus of the invention described above is so adapted that scattered light and fluorescent light from individual cells in a urine specimen is detected by flow cytometry, data indicative of scattered-light intensity and data indicative of fluorescent light intensity is obtained from the scattered light and fluorescent light, the scattered light is converted into pulse signals, and the pulse widths is converted into data indicative of cell diameter in accordance with known cell diameters. Furthermore, actual-measurement data indicating the characteristics of each cell is stored in memory beforehand as cell judgement values, and the data indicative of the detected cells is analyzed in accordance with these cell judgment values.

As a result, the cells contained in a urine specimen can be classified into erythrocytes, leukocytes, epithelial cells, casts and bacteria, etc., automatically.

Furthermore, all cells detected in the urine specimen can be enumerated and displayed as well as the counts of individual cell types in the urine specimen.

As many apparently widely different embodiments of the present invention can be made without departing from the spirit and scope thereof, it is to be understood that the invention is not limited to the specific embodiments thereof except as defined in the appended claims.

What is claimed is:

1. An apparatus for analyzing cells in urine, comprising:

first means for irradiating with light a constricted zone through which various cells contained in a urine specimen flow in single file, and detecting scattered light and fluorescent light emitted by individual cells, said individual cells having been stained with a stain such that DNA will specifically emit fluorescence, and said light having a light beam width in a direction of cell flow in the range of 1 μm to 20 μm;

a first photoelectric converting circuit for converting the scattered light detected by said first means into an electric signal output;

a second photoelectric converting circuit for converting the fluorescent light detected by said first means into an electric signal output;

second means for generating scattered-light intensity data based upon the electric signal output from said first photoelectric converting circuit;

third means for generating fluorescent light intensity data based upon the electric signal output from said second photoelectric converting circuit;

fourth means for converting the electric signal output from said first photoelectric converting circuit into pulse-width data;

fifth means for converting the pulse-width data obtained by said fourth means into cell diameter data;

memory means in which cell diameter information, scattered-light intensity information, and fluorescent light intensity information are stored in advance as cell judgment values, said cell judgment values being indicative of characteristics of different types of cells and obtained statistically upon carrying out actual measurement of various cells in urine, said cell judgment values establishing low, medium, and high levels for scattered-light intensity and fluorescent light intensity of said different types of cells; and sixth means for classifying cells in the urine specimen based upon the cell judgment values, such that:

(a) a cell is classified as an erythrocyte when the scattered-light intensity data of said second means is medium, the fluorescent light intensity data is low, and the cell diameter data is 3–10 μm;

(b) a cell is classified as a leucocyte when the scattered-light intensity data of said second means is medium, the fluorescent light intensity data is high, and the cell diameter data is 3–15 μm;

(c) a cell is classified as an epithelial when the scattered-light intensity data of said second means is medium or high, the fluorescent light intensity data is high, and the cell diameter data is 15–150 μm;

(d) a cell is classified as a cast when the scattered-light intensity data of said second means is medium, the fluorescent light intensity data is low or high, and the cell diameter data is greater than 100 μm; and (e) a cell is classified as a bacterium when the scattered-light intensity data of said second means is low, the fluorescent light intensity data is low or medium, and the cell diameter data is 1–3 μm.

2. The apparatus of claim 1, further comprising seventh means for counting the cells classified by said sixth means, and means for displaying cell classifications obtained by said sixth means and cell counts obtained by said seventh means.

3. A method for analyzing cells in urine, comprising the steps of:

irradiating with light a constricted zone through which various cells contained in a urine specimen flow in single file, said light having a light beam width in a direction of cell flow in the range of 1 μm to 20 μm;

detecting scattered light and fluorescent light emitted by individual cells, said individual cells having been stained with a stain such that DNA will specifically emit fluorescence;

converting the scattered light detected in the detecting step into an electric signal output using a first photoelectric converting circuit;

converting the fluorescent light detected in the detecting step into an electric signal output using a second photoelectric converting circuit;

generating scattered-light intensity data based upon the electric signal output from said first photoelectric converting circuit;

generating fluorescent light intensity data based upon the electric signal output from said second photoelectric converting circuit;

generating pulse width data from the electric signal output from the first photoelectric converting circuit;

converting the pulse-width data into cell diameter data;

providing a memory device in which cell judgment values have been stored in advance, said cell judgment values comprising cell diameter information, scattered-light intensity information, and fluorescent light intensity information, said cell judgment values being indicative of characteristics of different types of cells and obtained statistically by carrying out actual measurement of various cells in urine, said cell judgment values establishing low, medium, and high levels for scattered-light intensity and fluorescent light intensity of said different types of cells; and classifying each cell in the urine specimen based upon the cell judgment values, such that:

(a) a cell is classified as an erythrocyte when the scattered-light intensity data is medium, the fluorescent light intensity data is low, and the cell diameter data is 3–10 $\mu$m;

(b) a cell is classified as a leucocyte when the scattered-light intensity data is medium, the fluorescent light intensity data is high, and the cell diameter data is 3–10 $\mu$m;

(c) a cell is classified as an epithelial when the scattered-light intensity data is medium or high, the fluorescent light intensity data is high, and the cell diameter data is 15–150 $\mu$m;

(d) a cell is classified as a cast when the scattered-light intensity data is medium, the fluorescent light intensity data is low or high, and the cell diameter data is greater than 100 $\mu$m; and (e) a cell is classified as a bacterium when the scattered-light intensity data is low, the fluorescent light intensity data is low or medium, and the cell diameter data is 1–3 $\mu$m.

4. The method of claim 3, further comprising the steps of counting each of the cells classified in the classifying step and displaying cell classifications obtained in said classifying step and cell counts obtained in said counting step.

* * * * *